US00PP30915P3

(12) United States Plant Patent
Zamiri et al.

(10) Patent No.: US PP30,915 P3
(45) Date of Patent: Oct. 1, 2019

(54) POMEGRANATE TREE NAMED 'YAIN'

(50) Latin Name: ***Punica granatum* L.**
Varietal Denomination: YAIN

(71) Applicant: Zamiri Nurseries Ltd., Yesod Hama'ala, North Galilee (IL)

(72) Inventors: Yirmiyahu Zamiri, Yesod Hama'ala (IL); Nimrod Zamiri, Yesod Hama'ala (IL)

(73) Assignee: ZAMIRI NURSERIES LTD., Yesod Hama'Ala (IL)

( * ) Notice: Subject to any disclaimer, the term of this patent is extended or adjusted under 35 U.S.C. 154(b) by 0 days.

(21) Appl. No.: 15/732,618

(22) Filed: Dec. 5, 2017

(65) Prior Publication Data

US 2019/0174663 P1 Jun. 6, 2019

(51) Int. Cl.
*A01H 5/02* (2018.01)
*A01H 6/00* (2018.01)
*A01H 5/08* (2018.01)

(52) U.S. Cl.
USPC ..... Plt./210
CPC ..... *A01H 6/00* (2018.05); *A01H 5/08* (2013.01)

(58) Field of Classification Search
USPC ..... Plt./210
CPC ..... A01H 5/08; A01H 5/02
See application file for complete search history.

(56) References Cited

PUBLICATIONS

Printout of application information from PLUTO database for corresponding Israeli Plant Breeders' Rights application No. 4180 filed Dec. 14, 2008 (1 page) (retrieved from www.wipo.int/pluto).
Printout of application information from PLUTO database for corresponding CPVO Plant Breeders' Rights application No. 2017/1200 filed May 3, 2017 (1 page) (retrieved from www.wipo.int/pluto).
Printout of application information from PLUTO database for corresponding Australian Plant Breeders' Rights application No. 2017323 filed Oct. 24, 2017 (1 page) (retrieved from www.wipo.int/pluto).

*Primary Examiner* — Kent L Bell
(74) *Attorney, Agent, or Firm* — Foley & Lardner LLP

(57) ABSTRACT

A new and distinct pomegranate variety of *Punica granatum* named 'YAIN', particularly characterized by its large, slightly flattened fruit; shiny, medium red fruit color; soft, easy palatable seeds; mid-season ripening; and excellent taste.

6 Drawing Sheets

Botanical name of the genus and species of the plant claimed: *Punica granatum* L.
Variety denomination: 'YAIN'.

BACKGROUND OF THE INVENTION

The present invention relates to a new and distinct variety of pomegranate tree, botanically known as *Punica granatum* L. of the Lythraceae family, and hereinafter referred to by the variety denomination 'YAIN'.

The new *Punica granatum* 'YAIN' was discovered and selected by the inventors, Yirmiyahu Zamiri and Nimrod Zamiri, as a naturally-occurring whole plant mutation growing in a cultivated area in 2005 in Yesod Hama'ala, North Galilee, Israel. The new *Punica granatum* 'YAIN' was selected by the inventors based on large sized fruit, attractive fruit color and appearance, mid-season ripening and soft seed.

Asexual propagation of the new *Punica granatum* variety by cuttings, has demonstrated that the combination of characteristics as herein disclosed for the new variety are firmly fixed and retained through successive cycles of asexual propagation. The new variety propagates true-to-type.

BRIEF DESCRIPTION OF THE INVENTION

The following traits have been repeatedly observed and are determined to be unique characteristics of 'YAIN' which in combination distinguish this pomegranate tree as a new and distinct variety:

1. large, slightly flattened fruit;
2. shiny medium red fruit color;
3. soft, easy palatable seeds;
4. mid-season ripening; and
5. excellent taste.

Of the commercial varieties known to the present inventors, the most similar in comparison to the new *Punica granatum* 'YAIN' is *Punica granatum* variety 'WONDERFUL', unpatented, in the following characteristics described in Table 1

TABLE 1

Comparison with Similar Variety

| Characteristic | New Variety 'YAIN' | Comparison Variety 'WONDERFUL' (unpatented) |
|---|---|---|
| Fruit: shape | slightly flattened | round |
| Fruit: color | medium red (RHS 42A) | dark red (RHS 47A) |
| Fruit: glossiness | strong | weak |
| Seed: hardiness | soft | hard |

BRIEF DESCRIPTION OF THE PHOTOGRAPHS

The accompanying photographs illustrate the overall appearance of the new *Punica granatum* variety 'YAIN' showing the colors as true as is reasonably possible with colored reproductions of this type. Colors in the photographs may differ slightly from the color values cited in the detailed botanical description, which accurately describe the color of 'YAIN'.

Figure 1:
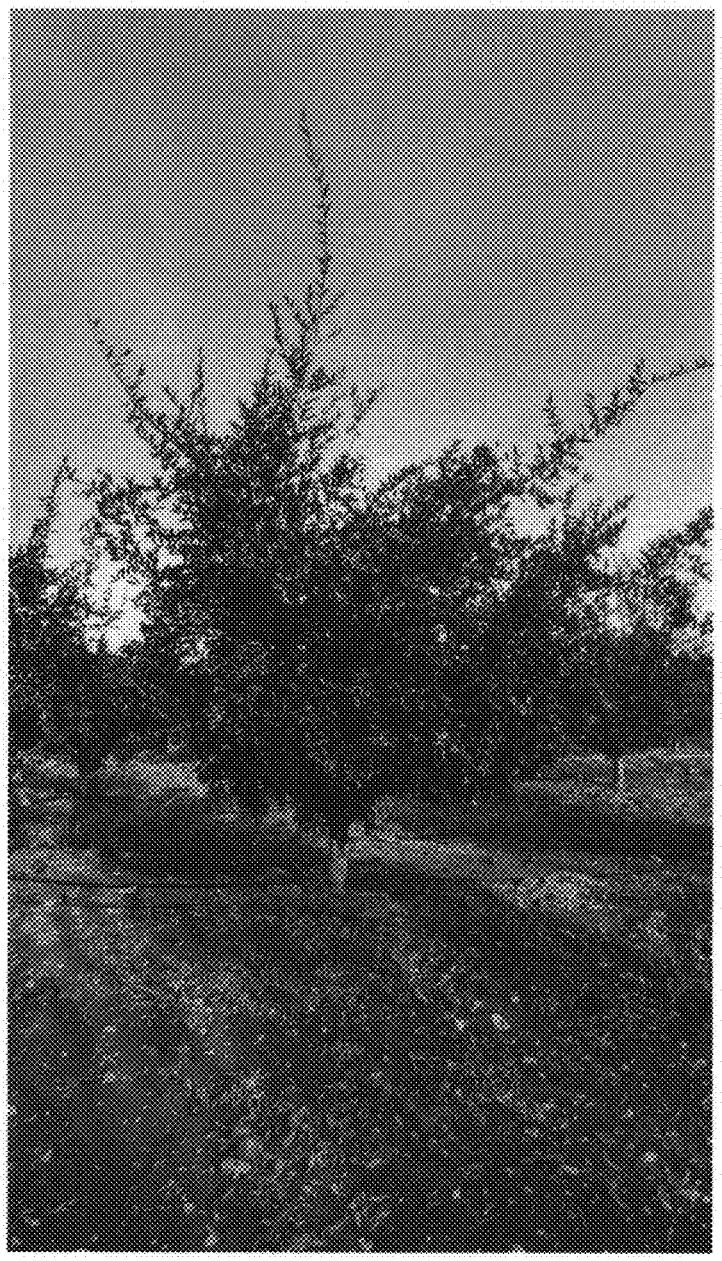
Figure 2:
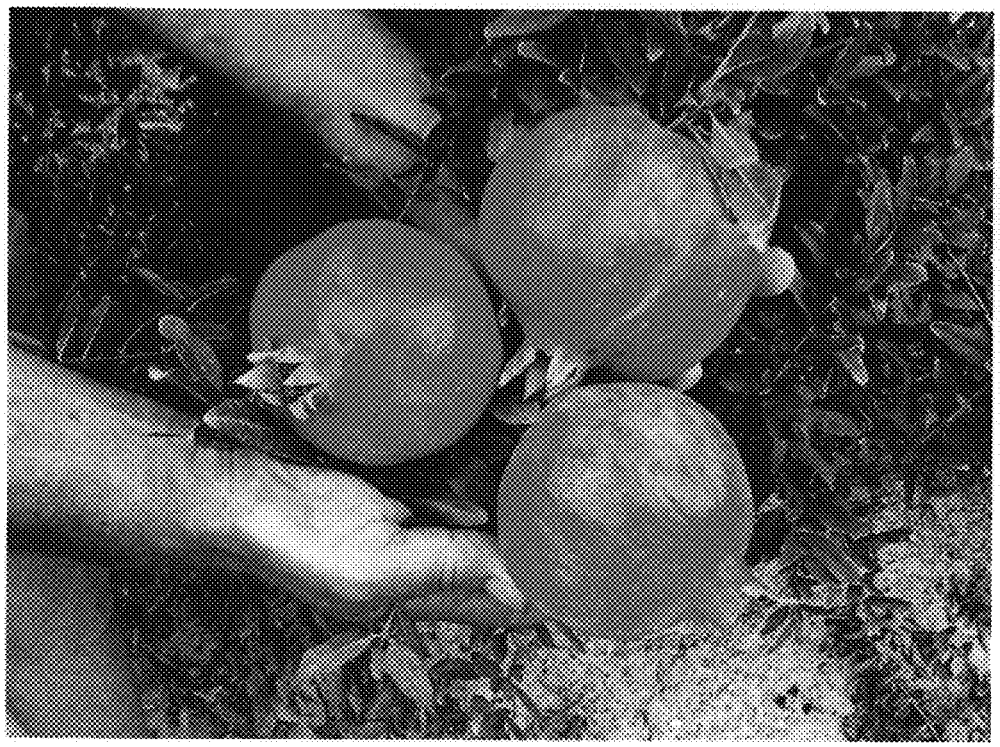
Figure 3:
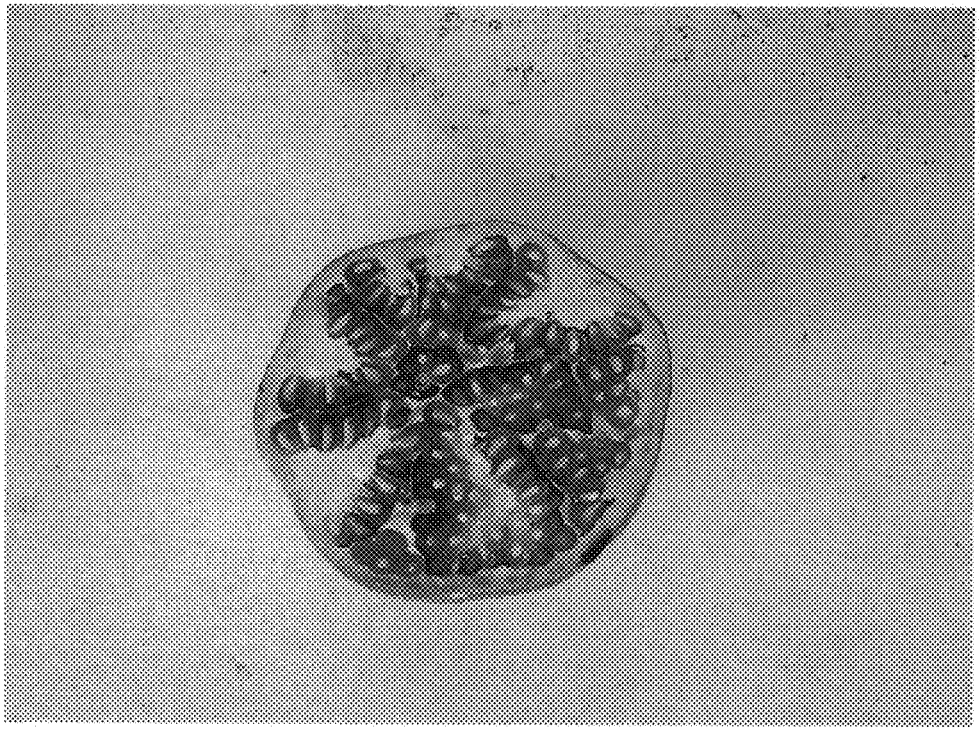
Figure 4:
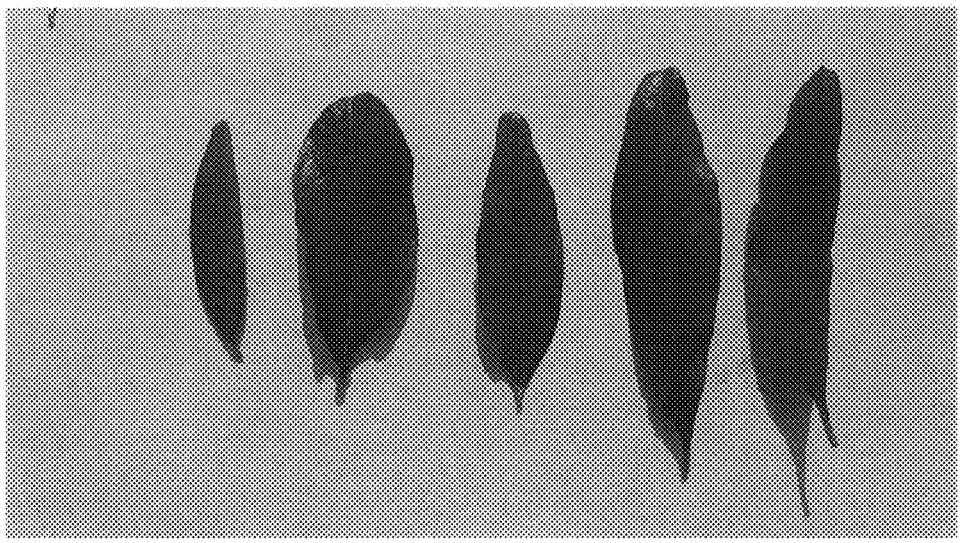
Figure 5:
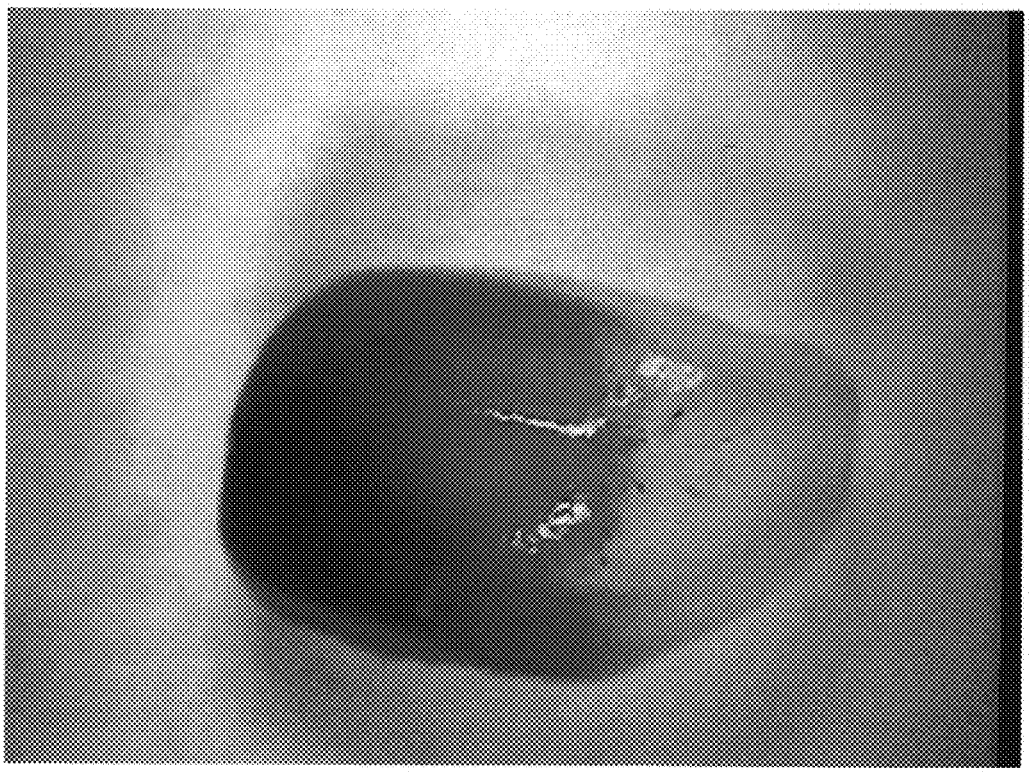
Figure 6:
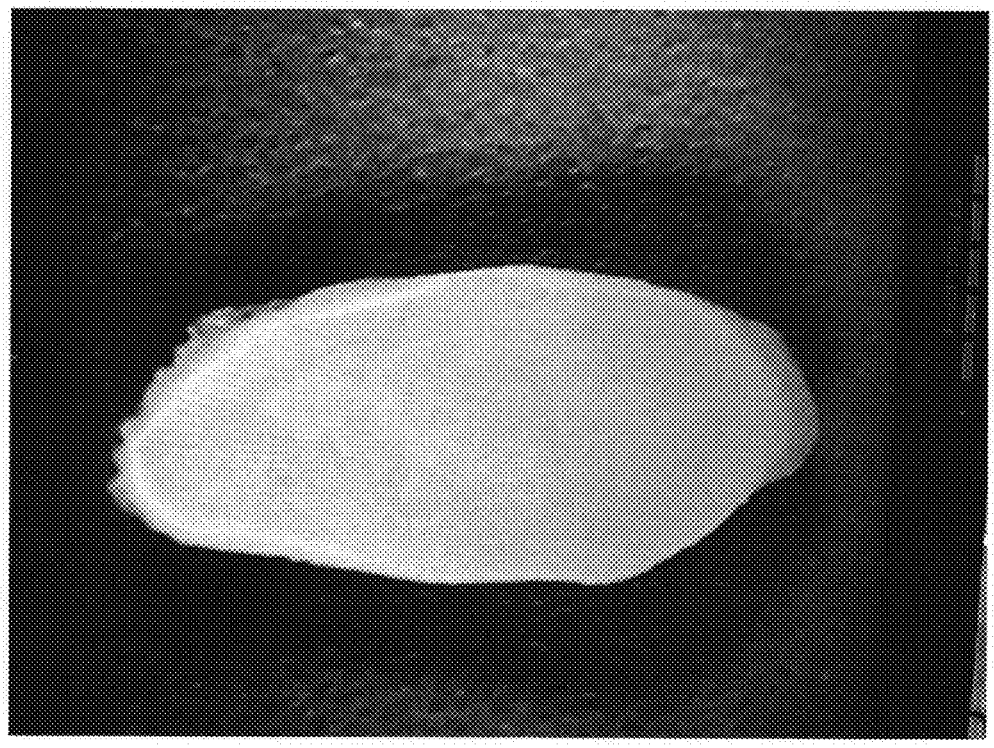

FIG. 1—shows a typical seven-year-old fruiting tree of 'YAIN';

FIG. 2—shows typical mature fruit of 'YAIN' on the tree;

FIG. 3—shows a cross section of the mature fruit of 'YAIN';

FIG. 4—shows typical leaves of 'YAIN';

FIG. 5—shows a typical aril of 'YAIN';

FIG. 6—shows a typical seed of 'YAIN';

DETAILED MORPHOLOGICAL DESCRIPTION

The new *Punica granatum* of 'YAIN' has not been observed under all possible environmental conditions. The phenotype of the new variety may vary with variations in environment such as temperature, light intensity, and day length without any change in the genotype of the pomegranate tree.

The aforementioned photographs, together with the following observations, measurements and values describe trees of of 'YAIN' as grown in the pomegranate orchard in Yesod Hama'ala, North Galilee, Israel, under conditions which closely approximate those generally used in commercial practice for soil, temperature, and fertilization.

Unless otherwise stated, the detailed botanical description includes observations, measurements and values based on 7-year old of 'YAIN' trees grown in the pomegranate orchard in Yesod Hama'ala, North Galilee, Israel. Quantified measurements are expressed as an average of measurements taken from a number of trees of of 'YAIN'. The measurements of any individual tree, or any group of trees, of the new variety may vary from the stated average.

Color references are made to The Royal Horticultural Society Colour Chart (R.H.S.), edition 2007, except where general colors of ordinary significance are used. Color values were taken under full sunlight conditions in Yesod Hama'ala, North Galilee, Israel.

All of the trees of 'YAIN', insofar as they have been observed, have been identical in all the characteristics described below.

Classification:

*Botanical.*—*Punica granatum* L.

Propagation: Rooted cuttings, year-round. Substrate half peat, half kokos; cuttings are dipped in a 2000 ppm IBA auxine.

Growing conditions: Annual average rainfall is 280 mm from October till March.

Soil: Red loam.

*Light intensities.*—Full sunlight.

*Temperature.*—During day in summer, grown in a range of 25° C. to 33° C., and during the night, grown in a range of 20° C. to 25° C. During day in winter, grown in a range of 5° C. to 20° C., and during the night, grown in a range of −2° C. to 10° C.

*Fertilization.*—10 kg/ha in first year after planting. Increased amounts in following years of a balanced fertilizer with level of NPK 10-1-18. Micro-elements: none applied. Pruning or trimming requirements: tillers are removed.

Tree:

*Age.*—Observed trees were 7 years old.

*Type.*—Deciduous.

*Bearing type.*—Yearly, no alternate bearing.

*Vigor.*—Very strong.

*Flowering time.*—Second week of March til end of April.

*Fruit maturity.*—End of August till mid-September.

*Form.*—Upright, globose with semi-erect branch angles.

*Habit.*—A medium-sized tree with one trunk and 5 main branches extending from the trunk at about 50 cm above ground level, diameter of trunk at 50 cm height from the ground is about 15 cm, crown is symmetrical spherical in shape.

*Branching habit.*—Main branches angle is semi-erect with respect to trunk, if allowed to grow naturally.

*Height.*—About 3 m.

*Spread.*—About 3 m.

*Trunk.*—Height (up to main branches): about 0.5 m. Diameter: about 15 cm.

*Color of bark.*—Brown, RHS 200 C, and grey-brown, RHS 199 D.

*Branches.*—Number per tree: five. Length: up to 3 m. Diameter (at 7 years): about 7 cm. Surface texture: medium rough. Pubescence: absent. Color: grey-brown, RHS 199 D. Mature, after about 2 years old, brown, RHS 200 C, and grey-brown, RHS 199 D. New growth: per growing season up to 2 m. RHS grey-brown RHS 199 B. Internode length: about 2 cm to 10 cm. Internode diameter: about 2 mm to 5 mm. Branch spines: Length: about 1.2-3.7 cm. Thickness: 1.5 mm. Color: medium brown RHS 177 B. Branch lenticels: none.

*Spurs.*—Present: yes. Distance between each spur: on the one-year old branches, the distance is about 2 mm to 5 cm. Diameter of each spur: about 3 mm. Length: 10-18 mm. Color: dark grey-brown RHS 199A. Number of fruit per spur: one or two.

Foliage:

*Arrangement.*—Opposite pairs, alternately crossing at right angles.

*Prickles.*—

*Position.*—In leaf axil and at tip of shoot.

*Length of prickle.*—1.2-3.7 cm.

*Thickness of base of prickle.*—1.5 mm.

*Color of prickle.*—Medium brown RHS 177 B.

*Fully grown leaf.*—

*Type.*—Simple.

*Lamina.*—Length: about 60-70 mm. Width: about 17-20 mm. Length/width ratio: 1.3. Overall shape: elliptic. Base shape: acute. Apex shape: rounded emarginated. Margin: entire, weakly undulated. Upper surface: glabrous, dark green RHS 141 A. Lower surface: glabrous, medium green RHS 141 C. Attitude in relation to shoot: outwards. Venation: midrib of upper surface: not visible. Color of midrib of lower surface: medium to dark red RHS 41 D. Petiole: Length: about 5-10 mm thickness: about 2 mm. Texture: smooth. Color: dark red RHS 53 C.

*Stipules.*—None.

*Glands.*—None.

Inflorescence:

*Flower.*—Arrangement: singly born. Number: one or two per spur.

*Bud*.—Shape: oblate. Length: 15-20 mm. Diameter: 10-15 mm. Color: dark red RHS 44 A.

*Flower*.—Type: single, trumpet-shaped hermaphrodite flower. Maximum diameter: around 50 mm. Fragrance: none. Length: 54-58 mm.

*Sepals*.—Number: five, six, or seven. Length about 10 mm. Width about 8 mm. General shape: triangular. Apex: acute. Base: fused. Outer surface texture: smooth. Inner surface texture: smooth. Margin: entire. Color of outer surface: dark to very dark red RHS 39 A. Color of inner surface: red RHS 42 A.

*Petals*.—Number per flower: five, six or seven. Length: about 30 mm. Maximum width: about 24 mm. Overall shape: broad elliptic. Shape of base: obtuse. Shape of apex: rounded. Margin: weakly undulated. Surface of upper side: glabrous. Surface of lower side: glabrous. Color of upper side: dark to very dark red RHS 39 A. Color of lower side: red RHS 42 A.

*Stamen*.—Number: numerous. Length of stamen: about 10 mm. Color of filament: very dark orange-red RHS 33 A. Color of anther. dark yellow RHS 7 B. Color of pollen. medium to dark yellow RHS 4 A. Amount of pollen: abundant

*Style*.—Length: about 8 mm. Color: light to medium red RHS 39 D.

*Stigma*.—Size: very small. Color: light green RHS 138B to RHS 138C.

*Pedicel*.—None; flower is sessile.

Fruit:

*Maturity when described*.—Ripe for commercial harvesting and consumption; about August 28 till September 15.

*Maturity period after full bloom*.—About 4 months after full flowering in the first week of May in Yesod Hama'ala, Northern Galilee, Israel.

*Date of first and last picking* (*harvest*).—From mid August till end of October in Yesod Hama'ala, Northern Galilee, Israel.

*Stalk*.—Not present

*Type*.—Berry. General shape: globose. Apex shape: slightly flattened. Base shape: flat. Suture: none. Average weight: about 400-600 g.

*Fruit size*.—Length: about 85-95 mm. Maximum diameter: about 100-120 mm. Position of maximum diameter: in middle. Ratio length/maximum diameter: 0.81. Color: red RHS 42 A.

*Calyx* (*crown*).—Length: about 25-30 mm. Diameter: about 24-28 mm. Length/diameter ratio: 0.9. Overall shape: cylindrical. Apex shape: triangular with acute tip. Apex length: 15-20 mm. Apex base: fused. Texture of upper surface: smooth. Texture of lower surface: smooth. Margin: entire. Attitude of apex: erect at maturity, curving outwards when stored. Color of crown: red RHS 42 A. Rind: Texture: smooth, rather leathery. Inside color: medium yellow RHS 4 B. Thickness: about 1.5 mm.

*Septum*.—Thickness: about 1 mm. Texture: smooth, firm, leathery. Color: medium yellow RHS 4 B. Flesh: None.

*Locules*.—Number: Predominantly five. Length: 80-90 mm. Width: 20-24 mm.

Arils:

*Number per fruit*.—Very numerous.

*Shape*.—Obconical.

*Length of aril*.—10 mm.

*Width of aril*.—8 mm.

*Thickness of aril*.—8 mm.

*Color of upper part of aril*.—Very dark red RHS 45 A.

*Color of lower part of aril*.—Opaque, milky.

*Flavor*.—No typical flavor observed.

*Seeds*.—One seed per aril.

*General shape*.—Ovoid.

*Shape of base*.—Rounded.

*Shape of apex*.—Obtuse.

*Surface*.—Smooth. Length: about 7 mm. Width: about 3 mm. Color at maturity: medium yellow RHS 4 B.

Market: Fresh market and food, juice and dietary supplement manufacturing.

Usage: Fruit and extract.

Disease/pest resistance: None observed.

Disease/pest susceptibility: None observed.

Winter hardiness: Tolerant to temperatures down to 3° C. without observed damage to wood and buds of dormant pomegranate trees.

Drought/heat tolerance: Tolerant to temperatures up to 35° C., growth is limited by drought periods without irrigation.

Shipping/storage characteristics: 'YAIN' can be stored in cold temperature conditions at 7° C. for about 6 weeks without loosing firmness and juiciness.

We claim:

1. A new and distinct variety of *Punica granatum* plant named 'YAIN', as illustrated and described herein.

* * * * *